(12) United States Patent
Meng et al.

(10) Patent No.: US 11,594,653 B2
(45) Date of Patent: Feb. 28, 2023

(54) FLAT PANEL DETECTOR AND MEDICAL IMAGE DETECTION DEVICE

(71) Applicant: BOE Technology Group Co., Ltd., Beijing (CN)

(72) Inventors: Fanli Meng, Beijing (CN); Jiangbo Chen, Beijing (CN); Zeyuan Li, Beijing (CN); Yao Lu, Beijing (CN); Ning Dang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 17/356,194

(22) Filed: Jun. 23, 2021

(65) Prior Publication Data
US 2022/0165900 A1 May 26, 2022

(30) Foreign Application Priority Data

Nov. 23, 2020 (CN) .......................... 202011321034.2

(51) Int. Cl.
*H01L 31/08* (2006.01)
*A61B 6/00* (2006.01)
*H01L 31/0224* (2006.01)

(52) U.S. Cl.
CPC .......... *H01L 31/085* (2013.01); *A61B 6/4208* (2013.01); *A61B 6/56* (2013.01); *H01L 31/0224* (2013.01)

(58) Field of Classification Search
CPC ............... H01L 31/085; H01L 31/0224; H01L 27/14676; A61B 6/4208; A61B 6/56
See application file for complete search history.

(56) References Cited

U.S. PATENT DOCUMENTS

2013/0168563 A1* 7/2013 Kim .................. H01L 27/14676 250/370.06
2017/0293037 A1* 10/2017 Schmidt ................ H01L 51/424

* cited by examiner

*Primary Examiner* — Kiho Kim
(74) *Attorney, Agent, or Firm* — Workman Nydegger

(57) ABSTRACT

The present disclosure provides a flat panel detector and a medical image detection device. The flat panel detector includes a base substrate, wherein the base substrate is divided into a plurality of detection units, each detection unit includes a first absorbing layer and a second absorbing layer, both of which are arranged on the base substrate in a laminating manner, the second absorbing layer is located on one side, away from the base substrate, of the first absorbing layer, and an energy level of rays absorbed by the second absorbing layer is smaller than that of rays absorbed by the first absorbing layer; a voltage supply electrode structure; and an output circuit, electrically connected to the voltage supply electrode structure and configured to output a first detection signal of the first absorbing layer and a second detection signal of the second absorbing layer.

12 Claims, 2 Drawing Sheets

FLAT PANEL DETECTOR AND MEDICAL IMAGE DETECTION DEVICE

CROSS-REFERENCE TO RELATED APPLICATION

This application is based on and claims priority under 35 U.S.C 119 to Chinese Patent Application No. 202011321034.2, filed on Nov. 23, 2020, in the China National Intellectual Property Administration. The entire disclosure of the above application is incorporated herein by reference.

FIELD

The present disclosure relates to the technical field of digital medical imaging, and in particular to a flat panel detector and a medical image detection device.

BACKGROUND

At present, a semiconductor flat panel detector has been extensively used as an optical detection and sensing part in the field of digital medical imaging. The current flat panel detector mainly includes two types: The first one is an indirect detector, which is generally made using an amorphous silicon TFT backplane technology in combination with an amorphous silicon PIN diode technology (or amorphous silicon CMOS in combination with c-Si PPD diode technology); and the second one is a direct detector.

SUMMARY

The present disclosure provides a flat panel detector, wherein the flat panel detector includes a base substrate, and the base substrate is divided into a plurality of detection units, each of the detection units include:

a first absorbing layer and a second absorbing layer, wherein the first absorbing layer and the second absorbing layer are arranged on the base substrate in a laminating manner, the second absorbing layer is located on one side, away from the base substrate, of the first absorbing layer, and an energy level of rays absorbed by the second absorbing layer is smaller than that of rays absorbed by the first absorbing layer;

a voltage supply electrode structure, configured to provide the corresponding first absorbing layer and the corresponding second absorbing layer with an operating voltage; and an output circuit, electrically connected to the corresponding voltage supply electrode structure and used for outputting a first detection signal of the corresponding first absorbing layer and a second detection signal of the corresponding second absorbing layer.

Optionally, the output circuit comprises a TFT arranged on the base substrate;

one side, away from the base substrate, of the TFT is sequentially provided with an interlayer insulating layer and a flat layer;

the voltage supply electrode structure comprises a bottom electrode, a first voltage supply top electrode and a second voltage supply top electrode, the bottom electrode, the first voltage supply top electrode and the second voltage supply top electrode are located on one side, away from the interlayer insulating layer, of the flat layer and are laminated sequentially; the first absorbing layer is located between the bottom electrode and the first voltage supply top electrode, and the second absorbing layer is located between the first voltage supply top electrode and the second voltage supply top electrode; and the bottom electrode is electrically connected to a source electrode of corresponding TFT.

Optionally, the output circuit comprises a first TFT and a second TFT, the first TFT and the second TFT are arranged on a same layer on the base substrate;

one side, away from the base substrate, of the first TFT and the second TFT is sequentially provided with an interlayer insulating layer and a first flat layer;

the voltage supply electrode structure comprises a first bottom electrode, a first top electrode, a second bottom electrode and a second top electrode, the first bottom electrode, the first top electrode, the second bottom electrode and the second top electrode are located on one side, away from the interlayer insulating layer, of the first flat layer and are sequentially laminated; a second flat layer is arranged between the first top electrode and the second bottom electrode, the first absorbing layer is located between the first bottom electrode and the first top electrode, and the second absorbing layer is located between the second bottom electrode and the second top electrode; and the first bottom electrode is electrically connected to a source electrode of the first TFT, and the second bottom electrode is electrically connected to a source electrode of the second TFT.

Optionally, the voltage supply electrode structure further comprises: a first connecting electrode arranged on a same layer as the first bottom electrode and a second connecting electrode arranged on a same layer as the first top electrode, wherein a third flat layer, arranged on a same layer as the first absorbing layer, is disposed between the first connecting electrode and the second connecting electrode; and the first connecting electrode is electrically connected to the source electrode of the second TFT through a first via hole, the second connecting electrode is electrically connected to the first connecting electrode through a second via hole, and the second bottom electrode is electrically connected to the second connecting electrode through a third via hole.

Optionally, the first absorbing layer and the second absorbing layer are made from different materials.

Optionally, the first absorbing layer and second absorbing layer are made from a same material, and a thickness of the first absorbing layer is greater than that of the second absorbing layer.

Optionally, the first absorbing layer is made from amorphous selenium, mercury iodide, cadmium zinc telluride, lead iodide or perovskite; and the second absorbing layer is made from amorphous selenium, mercury iodide, cadmium zinc telluride, lead iodide or perovskite.

Optionally, the voltage supply electrode structure is made from metal or ITO.

Optionally, in response to the voltage supply electrode structure being made from metal, the voltage supply electrode structure includes a single metal layer made from Mo, Ti, Al or Nd, or the voltage supply electrode structure includes a laminated metal layer made from Mo/AlNd/Mo, Ti/Al/Ti or MTD/Cu/MTD.

The present disclosure further provides a medical image detection device, the medical image detection device including any one of above flat panel detectors and a display device in a signal connection with the flat panel detector.

DETAILED DESCRIPTION OF THE EMBODIMENTS

Figure 1:
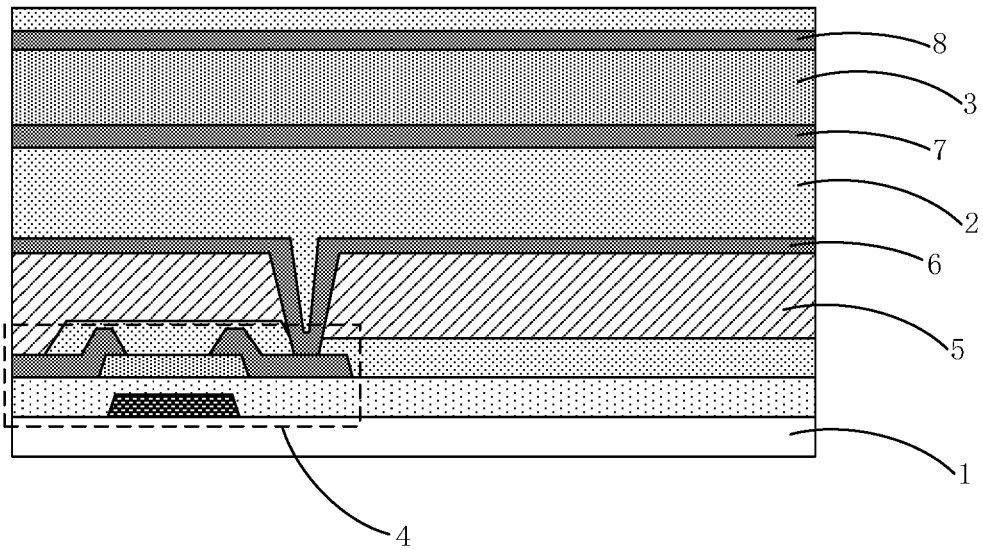
FIG. 1 is a partial cross-sectional schematic view of a flat panel detector provided by some embodiments of the present disclosure.

The technical solutions in the embodiments of the present disclosure will now be clearly and completely described with reference to the drawings in the embodiments of the present disclosure. Obviously, the embodiments described herein are only part of the embodiments of the present disclosure, not all of them. Based on the embodiments in the present disclosure, all other embodiments obtained by those of ordinary skill in the art without the exercise of inventive faculty fall within the protection scope of the present disclosure.

A thickness of an absorbing layer of the direct detector made from an X-ray sensitive material in the current market is fixed. Hence, high energy ray imaging applications (for example, the rays (≥70 kVp) for chest photography, orthopaedic photography and dental photography) may be compatible with low energy detection, but the low energy application detectors (for example, the rays (≤40 kVp) for mammography and soft tissue photography) may not be compatible with high energy ray detection. Moreover, photon energy is not distinguished when the detector detects the signals, so that dual-energy silhouette detection by means of single-exposure of a ray source cannot be realized. For this reason, what is needed now is a detector which is good in compatibility and convenient to facilitate dual-energy silhouette detection.

As shown in FIGS. 1-4, some embodiments of the present disclosure provides a flat panel detector, the flat panel detector including a base substrate 1, wherein the base substrate is divided into a plurality of detection units, each of detection units includes a first absorbing layer 2 and a second absorbing layer 3, the first absorbing layer and the second absorbing layer are arranged on the base substrate 1 in a laminating manner, the second absorbing layer is located on one side, away from the base substrate, of the first absorbing layer, and an energy level of rays absorbed by the second absorbing layer is smaller than that of rays absorbed by the first absorbing layer; a voltage supply electrode structure, configured to provide the corresponding first absorbing layer and the corresponding second absorbing layer with an operating voltage; and an output circuit, electrically connected to the corresponding voltage supply electrode structure and used for outputting a first detection signal of the corresponding first absorbing layer and a second detection signal of the corresponding second absorbing layer.

It should be noted that, in the flat panel detector, the following high energy rays refer to rays with high energy levels, which may be specifically X rays with high energy; the low energy rays refer to rays with low energy levels, which may be specifically X rays with low energy; the energy level of high energy rays is greater than that of low energy rays. The flat panel detector includes a base substrate, wherein the base substrate is divided into a plurality of detection units, each of detector units includes a first absorbing layer and a second absorbing layer, the first absorbing layer and the second absorbing layer are arranged on the base substrate in a laminating manner; the energy level of the rays that may be absorbed by the second absorbing layer is smaller than that of rays that may be absorbed by the first absorbing layer, that is, a wave length of rays that may be absorbed by the second absorbing layer is greater than that of rays that may be absorbed by the first absorbing layer, and the second absorbing layer is located on one side, away from the base substrate, of the first absorbing layer; the voltage supply electrode structure may provide the corresponding first absorbing layer with an interlayer operating voltage, so that electrons, generated after the corresponding first absorbing absorbs ray energy, move directionally to form a first detection signal, wherein the detection signal generated by absorption of the rays by the corresponding first absorbing layer is called the first detection signal; the voltage supply electrode structure may provide the corresponding second absorbing layer with an interlayer operating voltage, so that electrons, generated after the corresponding second absorbing layer absorbs ray energy, move directionally to form a second detection signal, wherein the detection signal generated by absorption of the rays by the corresponding second absorbing layer is called the second detection signal; each output circuit may be electrically connected to the corresponding voltage supply electrode structure to output the first detection signal of the corresponding first absorbing layer and the second detection signal of the corresponding second absorbing layer; the flat panel detector, has two absorbing layers capable of absorbing the rays with different kinds of energy, that is, may detect two types of rays with different kinds of energy. When low energy detection is conducted, that is, when the rays with low energy (for example, a common 25 kvp X-rays for examination of mammary glands or soft tissues) are used for exposure to realize detection, if the corresponding operating voltage may be applied to each second absorbing layer to output the corresponding second detection signal, the rays are used for forming a detection image after being processed according to the corresponding output second detection signal; when high energy detection is conducted, that is, when the rays with high energy are used (for example, common 80 kvp X-rays for chest X-ray film), if the corresponding operating voltage may be applied to each first absorbing layer to output the corresponding first detection signal, the rays are used for forming a detection image after being processed according to the output first detection signal; when the dual-energy silhouette detection is conducted, the dual-energy ray source may be used for exposure. It should be noted that the dual-energy ray source may simultaneously emit two types of rays with different kinds of energy, and may also simultaneously emit the rays within a wave band range, that is, may emit a variety of rays with different kinds of energy. The types of the rays emitted by the dual-energy rays will not be limited in the embodiment. When the exposure is enabled, the respective operating voltages of each first absorbing layer and each corresponding absorbing layer may be controlled to output the corresponding first and second detection signals, and a silhouette image signal, formed after each first detection signal and each second detection signal are subject to algorithmic processing, may be used for forming a silhouette image; and therefore, the flat panel detector in the embodiment is high in compatibility, and may realize dual-energy silhouette detection in a dual-energy ray exposure, and thus is convenient to use.

Accordingly, the flat panel detector, having the first and second absorbing layers capable of absorbing the rays with different kinds of energy, may detect the high energy rays and the low energy rays, and thus is good in compatibility;

and moreover, the detector may carry out the dual-energy silhouette detection in the same dual-energy ray exposure, and thus is convenient to use.

A variety of methods may be selected to arrange the output circuits and the voltage supply electrode structures, as follows.

Mode 1.

Figure 2:
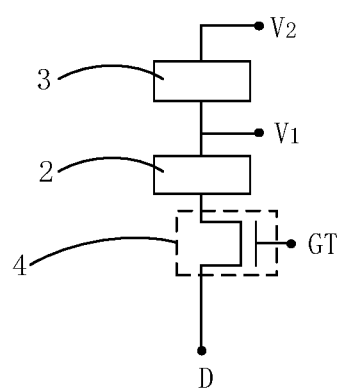
FIG. 2 is an equivalent schematic diagram of a circuit in one detection unit of a flat panel detector in FIG. 1.

As shown in FIGS. 1 and 2, wherein an end D in FIG. 2 expresses a drain electrode connecting end of each TFT, and in each of detection units, the output circuit includes a TFT 4 arranged on the base substrate; one side, away from the base substrate, of each TFT 4 is sequentially provided with an interlayer insulating layer and a flat layer 5, the interlayer insulating layer is arranged above the TFT 4 to cover the TFT 4, and the flat layer is arranged above the interlayer insulating layer to play a flattening role; each voltage supply electrode structure includes a bottom electrode 6, a first voltage supply top electrode 7 and a second voltage supply top electrode 8, all of which are located on one side, away from the corresponding interlayer insulating layer, of the corresponding flat layer and are sequentially laminated; each first absorbing layer 2 is located between the corresponding bottom electrode 6 and the corresponding first voltage supply top electrode 7, and each second absorbing layer 3 is located between the corresponding first voltage supply top electrode 7 and the corresponding second voltage supply top electrode 8; and each bottom electrode 6 is electrically connected to a source electrode of the corresponding TFT. Each of detection units includes a TFT arranged on the base substrate, the corresponding interlayer insulating layer and the corresponding flat layer are arranged above the each TFT, each bottom electrode is arranged on the corresponding flat layer and may penetrate through via holes of the corresponding interlayer insulating layer and the corresponding flat layer to electrically connect with a source electrode of the corresponding TFT; each bottom electrode is provided with the corresponding first absorbing layer, each first voltage supply top electrode is arranged above the corresponding first absorbing layer and may be electrically connected to a voltage supply circuit in the flat panel detector, and each voltage supply circuit may provide a voltage signal to the corresponding first voltage supply top electrode to offer the operating voltage to the corresponding first absorbing layer; each second absorbing layer is arranged above the corresponding first voltage supply top electrode, each second voltage supply top electrode is arranged above the corresponding second absorbing layer and may be electrically connected to the corresponding voltage supply circuit in the flat panel detector, and each voltage supply circuit may provide the corresponding second voltage supply top electrode with the voltage signal to offer the operating voltage to the corresponding second absorbing layer; in Method 1, each first absorbing layer is in a serial connection with the corresponding second absorbing layer; and moreover, in Method 1, as shown in FIGS. 1 and 2, the flat panel detector is used for high-energy detection, low energy detection or dual-energy silhouette detection respectively, including the following processes.

When the low energy detection is conducted, the low energy rays are used for exposure, that is, each voltage supply circuit may respectively provide a voltage signal V1 to the corresponding first voltage supply top electrode and a voltage signal V2 to the corresponding second voltage supply top electrode, so as to ensure that the corresponding first absorbing layer may be conducted while operating under the corresponding operating voltage thereof, and ensure the corresponding second absorbing layer to operate under the corresponding operating voltage thereof. By this time, each second absorbing layer may generate the corresponding second detection signal, each first absorbing layer may generate the corresponding first detection signal; and each TFT is enabled to read a superposed signal of the corresponding first and second absorbing layers on a gate (GT) thereof, and each superposed signal is processed to form a low energy detection signal; it should be noted that a small amount of the low energy rays will penetrate through the second absorbing layers, and then absorbed by the first absorbing layers; each first absorbing layer will generate a small amount of electrons and the corresponding detection signal which forms a compensatory detection signal, so as to form the corresponding superposed signal together with the corresponding second detection signal generated by each second absorbing layer, and each superposed signal is processed to form the low energy detection signal.

When the high energy detection is conducted, the high energy rays are used for exposure, so that each voltage supply circuit may respectively provide the voltage signal V1 to the corresponding first voltage supply top electrode and the voltage signal V2 to the corresponding second voltage supply top electrode, so as to ensure that the corresponding first electrode layer is operated under the corresponding operating voltage to generate the first detection signal, and ensure that the corresponding second absorbing layer may operate under the corresponding operating voltage thereof to generate the second detection signal; and each TFT is enabled to read the superposed signal of the corresponding first and second absorbing layers on the gate (GT) thereof, and the superposed signal is processed to form a high energy detection signal; or, each first absorbing layer may operate only, that is, the corresponding first voltage supply top electrode is disconnected such that no voltage signal is applied, and each voltage signal V1 is applied to the corresponding first voltage supply top electrode such that the corresponding first absorbing layer is operated only; and each TFT is enabled to read the first detection signal on the gate (GT) thereof, and each first detection signal forms the high energy detection signal. It should be noted that each generated compensatory detection signal is rather small and has a small effect on the corresponding first detection signal on account that each second absorbing layer absorbs a small amount of high energy rays. Therefore, when the high energy detection is conducted, the first and second absorbing layers may be controlled to operate simultaneously to obtain the high energy detection signals, or each first absorbing layer may be also controlled to operate only so as to obtain the high energy detection signal. Any method may be selected according to the actual detection conditions, without limitation in the embodiment.

When the dual-energy silhouette detection is conducted, the dual-energy ray source is used for exposure. During the exposure, each voltage signal V1 is provided to the corresponding first voltage supply top electrode, and then each second voltage supply top electrode is disconnected such that no voltage signal is applied, and thus the corresponding first absorbing layer is operated; each second absorbing layer will absorb the low energy rays, but will not generate an electrical signal; each TFT is enabled to read the first detection signal on the gate (GT) thereof to form a first dual-energy detection signal; then, each voltage signal V1 is provided to the corresponding first voltage supply top electrode, and each voltage signal V2 is provided to the corresponding second voltage supply top electrode, so that the corresponding first and second absorbing layers operate simultaneously in such a manner that the first absorbing layer generates the first detection signals and the second absorbing layer generates the second detection signals; and each TFT is enabled to read the superposed signals of the corresponding first and second absorbing layers on the gate (GT) thereof, and each superposed signal is processed to form a second dual-energy detection signal; or, the voltage signals are applied to the first and second voltage supply top electrodes in the meantime such that the first and second absorbing layers operate, namely, each first absorbing layer generates the corresponding first detection signal, and each second absorbing layer generates the corresponding second detection signal; each TFT is enabled to read the superposed signals of the corresponding first and second absorbing layers on the gate (GT) thereof, and each superposed signal is processed to form the second dual-energy detection signal, and then a voltage signal input of the corresponding second voltage supply top electrode is disconnected such that each first absorbing layer is operated; and each TFT is enabled to read the first detection signal on the gate (GT) thereof to form the first dual-energy detection signal; the first and second dual-energy detection signals may be calculated to form the silhouette signals, so as to input into the corresponding display device to form the silhouette image.

The above is that the first and second absorbing layers are arranged in a serial connection mode to provide the output circuits and the voltage supply electrode structures as well as controlled under different test conditions. The output circuits and the voltage supply electrode structures are simple to provide structurally and convenient in control method; and moreover, the dual-energy detection of the flat panel detector may be realized, the compatibility is good, and the detection signal accuracy is high.

Mode 2.

Figure 3:
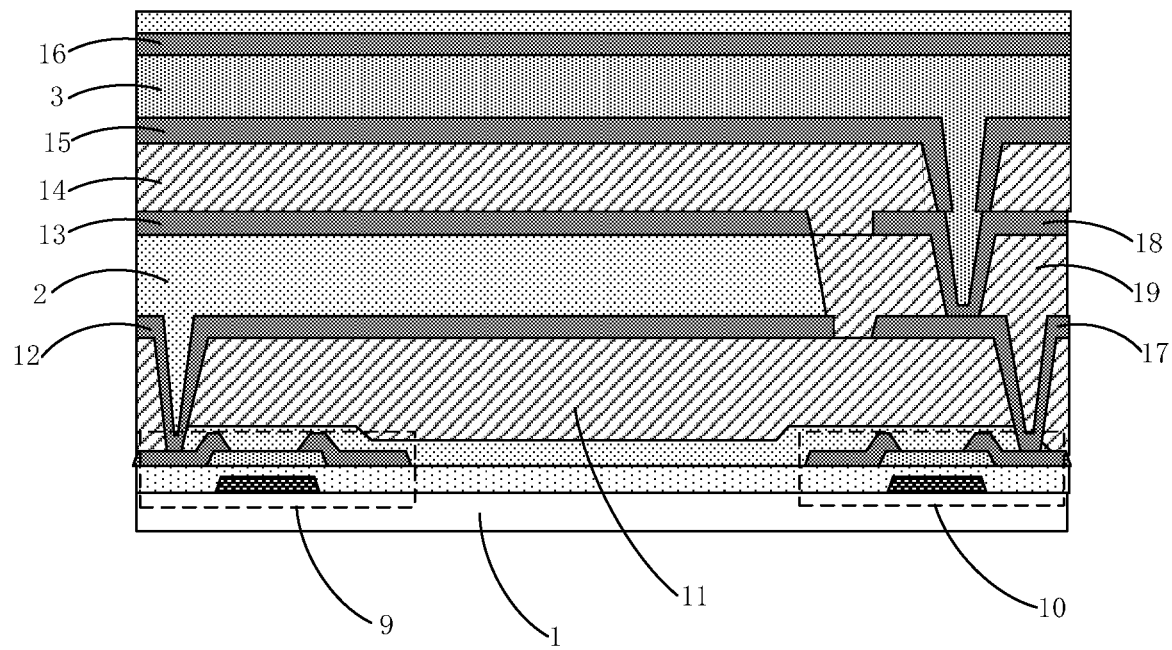
FIG. 3 is a partial cross-sectional schematic view of a flat panel detector provided by some embodiments of the present disclosure.
Figure 4:
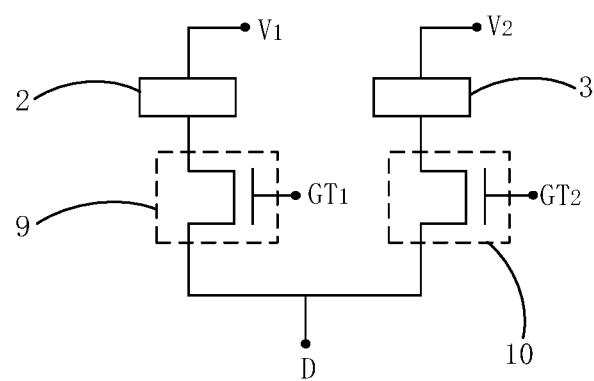
FIG. 4 is an equivalent schematic diagram of a circuit in one detection unit of a flat panel detector in FIG. 3.

As shown in FIGS. 3 and 4, an end D in FIG. 4 expresses a connecting end between each first TFT drain electrode and a corresponding second TFT drain electrode. Each output circuit includes a first TFT 9 and a second TFT 10, both of which are arranged on the same layer on the base substrate 1; one side, away from the base substrate, of each of the first TFTs 9 and the second TFTs 10 is sequentially provided with an interlayer insulating layer and a first flat layer 11, both of which are superposed, each interlayer insulating layer is arranged above the corresponding first TFT 9 and the corresponding second TFT 10 to cover the corresponding first TFT 9 and the corresponding second TFT 10, and each first flat layer is arranged on the corresponding interlayer insulating layer to play a flattening role; each voltage supply electrode structure includes a first bottom electrode 12, a first top electrode 13, a second bottom electrode 15 and a second top electrode 16, all of which are located on one side, away from the corresponding interlayer insulating layer, of the corresponding first flat layer 11 and are sequentially laminated; a second flat layer 14 is arranged between the corresponding first top electrode 13 and the corresponding second bottom electrode 15, each first absorbing layer 2 is located between the corresponding first bottom electrode 12 and the corresponding first top electrode 13, and each second absorbing layer 3 is located between the corresponding second bottom electrode 15 and the corresponding second top electrode 16; and each first bottom electrode 12 is electrically connected to a source electrode of the corresponding first TFT 9, and each second bottom electrode 15 is electrically connected to a source electrode of the corresponding second TFT 10. In each detection unit, each output circuit includes two TFTs, namely the first TFT and the second TFT, each interlayer insulating layer and each first flat layer are arranged above the corresponding first TFT and the corresponding second TFT, and the first flat layer is provided with the corresponding first bottom electrode which penetrates through via holes of the corresponding first flat layer and the corresponding interlayer insulating layer to electrically connect with the source electrode of the corresponding first TFT; each first bottom electrode is provided with the corresponding first absorbing layer provided with the corresponding first top electrode, and the corresponding first top electrode is electrically connected to the corresponding voltage supply circuit in the flat panel detector; each voltage supply circuit may provide the corresponding first top electrode with the voltage signal such that the corresponding first absorbing layer operates under the corresponding operating voltage thereof to generate the first detection signal; each first top electrode is provided with the corresponding second flat layer on which the corresponding second bottom electrode is arranged, each second bottom electrode is electrically connected to the source electrode of the corresponding second TFT, and the second and first bottom electrodes and the first top electrodes are arranged in an insulating manner; each second bottom electrode is provided with the corresponding second absorbing layer on which the corresponding second top electrode is arranged, and each second top electrode is electrically connected to the voltage supply circuit in the flat panel detector; each voltage supply circuit may provide the corresponding second top electrode with the voltage signal such that the corresponding second absorbing layer operates under the corresponding operating voltage thereof to generate the second detection signal; in Method 2, each first absorbing layer is in a parallel connection with the corresponding second absorbing layer; and moreover, in Method 2, as shown in FIGS. 3 and 4, the flat panel detector is used for high energy detection, low energy detection or dual-energy silhouette detection respectively, including the following processes.

When the low energy detection is conducted, the low energy rays are used for exposure, so that each voltage signal V2 may be provided to the corresponding second top electrode, and no voltage signal is applied to each first top electrode such that the corresponding second absorbing layer is operated only; and each second TFT is enabled to read the corresponding second detection signal on the gate (GT2) thereof to form a low energy detection signal; or, when each voltage signal V2 is provided to the corresponding second top electrode, each voltage signal V1 is provided to the corresponding first top electrode such that the corresponding first and second absorbing layers are operated, namely, each first absorbing layer generates the corresponding first detection signal, and each second absorbing layer generates the corresponding second detection signal; each first TFT is enabled to read the corresponding first detection signal on a gate (GT1) thereof, and each second TFT is enabled to read the corresponding second detection signal on a gate (GT2) thereof; and a superposed signal is formed by each first detection signal, as a compensation signal, and the corresponding second detection signal, and is processed to form a low energy detection signal.

When the high energy detection is conducted, the high energy rays are used for exposure, so that each voltage signal V1 may be provided to the corresponding first top electrode, and no voltage signal is applied to each second top electrode such that the corresponding first absorbing layer is operated only; and each first TFT is enabled to read the corresponding first detection signal on the gate (GT1) thereof to form a high energy detection signal; or, when each voltage signal V1 is provided to the corresponding first top electrode, and each voltage signal V2 is provided to the corresponding second top electrode such that the first and second absorbing layers are operated, namely, each first absorbing layer generates the corresponding first detection signal, and each second absorbing layer generates the corresponding second detection signal; each first TFT is enabled to read the corresponding first detection signal on the gate (GT1) thereof, and each second TFT is enabled to read the corresponding second detection signal on the gate (GT2) thereof; and a superposed signal is formed by each second detection signal, as a compensation signal, and the corresponding first detection signal, and is processed to form a high energy detection signal.

When the dual-energy silhouette detection is conducted, each voltage signal V1 may be provided to the corresponding first top electrode, no voltage signal is applied to each second top electrode such that the corresponding first absorbing layer is operated only; each first TFT is enabled to read the corresponding first detection signal on the gate (GT1) thereof to form a first dual-energy detection signal, and then the voltage signal input of each first top electrode is disconnected such that no voltage signal is applied to the corresponding first top electrode, and each voltage signal V2 is applied to each second top electrode such that the corresponding second absorbing layer is operated only; and each second TFT is enabled to read the corresponding second detection signal on the gate (GT2) thereof, so as to form a second dual-energy detection signal; or, the voltage signal input of each first top electrode is disconnected such that no voltage signal is applied to the first top electrodes, and each voltage signal V2 is applied to each second top electrode such that the corresponding second absorbing layer is operated; each second TFT is enabled to read the corresponding second detection signal on the gate (GT2) thereof so as to form the first dual-energy detection signal; and then, each voltage signal V1 is provided to the corresponding first top electrode such that no voltage signal is applied to the corresponding second top electrode, and thus each first absorbing layer is operated only; each first TFT is enabled to read the corresponding first detection signal on the gate (GT1) thereof so as to form the first dual-energy detection signal; and the respective operating sequence of the first and second absorbing layers may be specifically set according to the actual conditions, which will not be limited in the embodiment; the obtained first and second dual-energy detection signals may be calculated to form silhouette signals, so as to input into the corresponding display device to form a silhouette image.

The above is that the first and second absorbing layers are arranged in a parallel connection mode to provide the output circuits and the voltage supply electrode structures as well as controlled under different test conditions. The output circuits and the voltage supply electrode structures are simple to provide structurally and convenient in control method; and moreover, the dual-energy detection of the flat panel detector may be realized, the compatibility is good, and the detection signal accuracy is high.

In the Mode 2, as shown in FIG. 3, each voltage supply electrode structure further includes: a first connecting electrode 17 arranged on the same layer as the corresponding first bottom electrode 12 and a second connecting electrode 18 arranged on the same layer as the corresponding first top electrode 13; the first connecting electrodes 17 and the first bottom electrodes 12 are arranged in an insulating manner, the second connecting electrodes 18 and the first top electrodes 13 are arranged in an insulating manner, and a third flat layer 19, arranged on the same layer as each first absorbing layer 2, is disposed between the corresponding first connecting electrode 17 and the corresponding second connecting electrode 18; each first connecting electrode 17 is electrically connected to the source electrode of the corresponding second TFT 10 through a first via hole, each second connecting electrode 18 is electrically connected to the corresponding first connecting electrode 17 through a second via hole, each second bottom electrode is electrically connected to the corresponding second connecting electrode through a third via hole and each second bottom electrode is electrically connected to the source electrode of the corresponding second TFT 10 through the corresponding first and second connecting electrodes, thus realizing stable connection and strong reliability.

Optionally, in the flat panel detector, materials of the first and second absorbing layers may be set as follows: the first and second absorbing layers are made from different materials; on account that the absorbing layers made from different materials have different abilities to absorb the rays, the first and second absorbing layers are made from different materials, which may ensure that the first and second absorbing layers are set to be as thin as possible under the conditions meeting the test when an energy level of the rays absorbed by the first absorbing layers is greater than that of the rays absorbed by the second absorbing layers, thus being beneficial for decreasing an overall thickness of the flat panel detector and realizing a thin and light design.

Alternatively, the first and second absorbing layers are made from a same material, and a thickness of each first absorbing layer is greater than that of the corresponding second absorbing layer.

Optionally, in the flat panel detector, each first absorbing layer is made from a photoconductor material such as amorphous selenium, mercury iodide, cadmium zinc telluride, lead iodide or perovskite; and the second absorbing layer is made from photoconductor materials including amorphous selenium, mercury iodide, cadmium zinc telluride, lead iodide or perovskite.

Optionally, in the flat panel detector, each voltage supply electrode structure is made from metal or ITO. Moreover, each voltage supply electrode structure, made from metal, may be a single metal layer made from Mo, Ti, Al or Nd, or the voltage supply electrode structure may be a laminated metal layer made from Mo/AlNd/Mo, Ti/Al/Ti or MTD/Cu/MTD. Each voltage supply electrode structure may be specifically set according to the actual conditions, which is not limited in embodiments.

Some embodiments of the present disclosure further provide an image detection device, including any one of dual-layer flat panel detectors provided by the technical solutions and a display device in a signal connection with the dual-layer flat panel detector.

It will be apparent to those skilled in the art that various amendments and variations may be made to the present disclosure without departing from the spirit and scope of the present disclosure. In this way, if these amendments and variations of the present disclosure are within the ranges of the claims of the present disclosure and equivalent technologies thereof, the present disclosure has also intended to contain those amendments and modifications.

What is claimed is:

1. A flat panel detector, comprising a base substrate, and the base substrate is divided into a plurality of detection units, each of the detection units comprises:
   a first absorbing layer and a second absorbing layer, wherein the first absorbing layer and the second absorbing layer are arranged on the base substrate in a laminating manner, the second absorbing layer is located on one side, away from the base substrate, of the first absorbing layer, and an energy level of rays absorbed by the second absorbing layer is smaller than that of rays absorbed by the first absorbing layer;

a voltage supply electrode structure, configured to provide the corresponding first absorbing layer and the corresponding second absorbing layer with an operating voltage; and an output circuit, electrically connected to the corresponding voltage supply electrode structure and used for outputting a first detection signal of the corresponding first absorbing layer and a second detection signal of the corresponding second absorbing layer;

wherein the output circuit comprises a first TFT and a second TFT, the first TFT and the second TFT are arranged on a same layer on the base substrate;

one side, away from the base substrate, of the first TFT and the second TFT is sequentially provided with an interlayer insulating layer and a first flat layer;

the voltage supply electrode structure comprises a first bottom electrode, a first top electrode, a second bottom electrode and a second top electrode, the first bottom electrode, the first top electrode, the second bottom electrode and the second top electrode are located on one side, away from the interlayer insulating layer, of the first flat layer and are sequentially laminated; a second flat layer is arranged between the first top electrode and the second bottom electrode, the first absorbing layer is located between the first bottom electrode and the first top electrode, and the second absorbing layer is located between the second bottom electrode and the second top electrode; and the first bottom electrode is electrically connected to a source electrode of the first TFT, and the second bottom electrode is electrically connected to a source electrode of the second TFT;

the voltage supply electrode structure further comprises: a first connecting electrode arranged on a same layer as the first bottom electrode and a second connecting electrode arranged on a same layer as the first top electrode, wherein a third flat layer, arranged on a same layer as the first absorbing layer, is disposed between the first connecting electrode and the second connecting electrode; and the first connecting electrode is electrically connected to the source electrode of the second TFT through a first via hole, the second connecting electrode is electrically connected to the first connecting electrode through a second via hole, and the second bottom electrode is electrically connected to the second connecting electrode through a third via hole.

2. The flat panel detector according to claim 1, wherein the first absorbing layer and the second absorbing layer are made from different materials.

3. The flat panel detector according to claim 2, wherein the first absorbing layer is made from amorphous selenium, mercury iodide, cadmium zinc telluride, lead iodide or perovskite; and the second absorbing layer is made from amorphous selenium, mercury iodide, cadmium zinc telluride, lead iodide or perovskite.

4. The flat panel detector according to claim 1, wherein the first absorbing layer and the second absorbing layer are made from a same material, and a thickness of the first absorbing layer is greater than a thickness of the second absorbing layer.

5. The flat panel detector according to claim 1, wherein the voltage supply electrode structure is made from metal or ITO.

6. The flat panel detector according to claim 5, wherein in response to the voltage supply electrode structure being made from metal, the voltage supply electrode structure comprises a single metal layer made from Mo, Ti, Al or Nd, or the voltage supply electrode structure comprises a laminated metal layer made from Mo/AlNd/Mo, Ti/Al/Ti or MTD/Cu/MTD.

7. A medical image detection device, comprising a flat panel detector and a display device in a signal connection with the flat panel detector, wherein the flat panel detector comprises a base substrate, and the base substrate is divided into a plurality of detection units, each of the detection units comprises:

a first absorbing layer and a second absorbing layer, wherein the first absorbing layer and the second absorbing layer are arranged on the base substrate in a laminating manner, the second absorbing layer is located on one side, away from the base substrate, of the first absorbing layer, and an energy level of rays absorbed by the second absorbing layer is smaller than that of rays absorbed by the first absorbing layer;

a voltage supply electrode structure, configured to provide the corresponding first absorbing layer and the corresponding second absorbing layer with an operating voltage; and an output circuit, electrically connected to the corresponding voltage supply electrode structure and used for outputting a first detection signal of the corresponding first absorbing layer and a second detection signal of the corresponding second absorbing layer;

wherein the output circuit comprises a first TFT and a second TFT, the first TFT and the second TFT are arranged on a same layer on the base substrate;

one side, away from the base substrate, of the first TFT and the second TFT is sequentially provided with an interlayer insulating layer and a first flat layer;

the voltage supply electrode structure comprises a first bottom electrode, a first top electrode, a second bottom electrode and a second top electrode, the first bottom electrode, the first top electrode, the second bottom electrode and the second top electrode are located on one side, away from the interlayer insulating layer, of the first flat layer and are sequentially laminated; a second flat layer is arranged between the first top electrode and the second bottom electrode, the first absorbing layer is located between the first bottom electrode and the first top electrode, and the second absorbing layer is located between the second bottom electrode and the second top electrode; and the first bottom electrode is electrically connected to a source electrode of the first TFT, and the second bottom electrode is electrically connected to a source electrode of the second TFT;

the voltage supply electrode structure further comprises: a first connecting electrode arranged on a same layer as the first bottom electrode and a second connecting electrode arranged on a same layer as the first top electrode, wherein a third flat layer, arranged on a same layer as the first absorbing layer, is disposed between the first connecting electrode and the second connecting electrode; and the first connecting electrode is electrically connected to the source electrode of the second TFT through a first via hole, the second connecting electrode is electrically connected to the first connecting electrode through a second via hole, and the second bottom electrode is electrically connected to the second connecting electrode through a third via hole.

8. The medical image detection device according to claim 7, wherein the first absorbing layer and the second absorbing layer are made from different materials.

9. The medical image detection device according to claim 8, wherein the first absorbing layer is made from amorphous selenium, mercury iodide, cadmium zinc telluride, lead iodide or perovskite; and the second absorbing layer is made from amorphous selenium, mercury iodide, cadmium zinc telluride, lead iodide or perovskite.

10. The medical image detection device according to claim 7, wherein the first absorbing layer and the second absorbing layer are made from a same material, and a thickness of the first absorbing layer is greater than a thickness of the second absorbing layer.

11. The medical image detection device according to claim 7, wherein the voltage supply electrode structure is made from metal or ITO.

12. The medical image detection device according to claim 11, wherein in response to the voltage supply electrode structure being made from metal, the voltage supply electrode structure comprises a single metal layer made from Mo, Ti, Al or Nd, or the voltage supply electrode structure comprises a laminated metal layer made from Mo/AlNd/Mo, Ti/Al/Ti or MTD/Cu/MTD.

\* \* \* \* \*